US00PP27944P2

(12) United States Plant Patent
Hartman

(10) Patent No.: US PP27,944 P2
(45) Date of Patent: Apr. 25, 2017

(54) ***CALADIUM* PLANT NAMED 'JPD 153-20'**

(50) Latin Name: *Caladium×hortulanum*
Varietal Denomination: JPD 153-20

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 14/998,539

(22) Filed: Jan. 16, 2016

(51) Int. Cl.
*A01H 5/02* (2006.01)

(52) U.S. Cl.
USPC ..... Plt./373

(58) Field of Classification Search
USPC ..... Plt./373
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Caladium* plant named 'JPD 153-20', characterized by its compact, short to intermediate in height, upright and uniformly mounded plant habit; moderately vigorous growth habit and rapid growth rate; fancy type leaves that are glossy and bright red in color with dark green-colored margins; and above average tolerance to *Xanthomonas* Leaf Spot.

4 Drawing Sheets

Botanical designation: *Caladium×hortulanum.*
Cultivar denomination: 'JPD 153-20'.

BACKGROUND OF THE INVENTION

The present invention relates to a new and distinct cultivar of *Caladium* plant, botanically known as *Caladium×hortulanum*, commercially referred to as a fancy leaf-type *Caladium* and hereinafter referred to by the name 'JPD 153-20'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2010 in Avon Park, Fla. of *Caladium×hortulanum* 'Blaze', not patented, as the female, or seed, parent with *Caladium×hortulanum* 'John Peed', not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2011.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since April, 2012 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'JPD 153-20'. These characteristics in combination distinguish 'JPD 153-20' as a new and distinct *Caladium* plant:

1. Compact, short to intermediate in height, upright and uniformly mounded plant habit.
2. Moderately vigorous growth habit and rapid growth rate.
3. Fancy type leaves that are glossy and bright red in color with dark green-colored margins.
4. Above average tolerance to *Xanthomonas* Leaf Spot.

Plants of the new *Caladium* differ primarily from plants of the female parent, 'Blaze', in the following characteristics:

1. Plants of the new *Caladium* and 'Blaze' differ in leaf color as leaves of 'Blaze' are dark green in color with burgundy red-colored venation and centers. Overall, leaves of plants of the new *Caladium* are more intense in color than leaves of 'Blaze'.
2. Plants of the new *Caladium* and 'Blaze' differ in leaf petiole color as leaf petioles of 'Blaze' are tan pink and dark brownish green in color.

Plants of the new *Caladium* differ primarily from plants of the male parent, 'John Peed', in the following characteristics:

1. Plants of the new *Caladium* and 'John Peed' differ in leaf color as leaves of 'John Peed' have dark red-colored centers and red-colored venation with dark green-colored margins. Overall, leaves of plants of the new *Caladium* are more intense in color than leaves of 'John Peed'.
2. Plants of the new *Caladium* and 'John Peed' differ in leaf petiole color as leaf petioles of 'John Peed' are dark pink with dark green to close to black-colored stippling and streaks.

Plants of the new *Caladium* can be compared to plants of *Caladium×hortulanum* 'Frieda Hemple', not patented. In side-by-side comparisons, plants of the new *Caladium* differ primarily from plants of 'Frieda Hemple' in the following characteristics:

1. Plants of the new *Caladium* are shorter than plants of 'Frieda Hemple'.
2. Leaves of plants of the new *Caladium* are glossy in luster whereas leaves of 'Frieda Hemple' are mostly dull in luster.
3. Plant of the new *Caladium* and 'Frieda Hemple' differ in leaf petiole color as leaf petioles of 'Frieda Hemple' are dark brownish green, close to black, in color.

Plants of the new *Caladium* can be compared to plants of *Caladium×hortulanum* 'Postman Joyner', not patented. In side-by-side comparisons, plants of the new *Caladium* differ primarily from plants of 'Postman Joyner' in the following characteristics:

1. Plants of the new *Caladium* are shorter than plants of 'Postman Joyner'.
2. Leaves of plants of the new *Caladium* are glossier in luster than leaves of 'Postman Joyner'.
3. Plants of the new *Caladium* and 'Postman Joyner' differ in leaf color as leaves of 'Postman Joyner' are dark green in color with bright red-colored centers.
4. Plants of the new *Caladium* and 'Postman Joyner' differ in leaf petiole color as leaf petioles of 'Postman Joyner' are close to black in color.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'JPD 153-20' in a container and grown in a shadehouse (tuber not de-eyed).

The photograph at the top of the second sheet is a comparison view of typical potted plants of the female parent, 'Blaze' (left), 'JPD 153-20' (center) and the male parent, 'John Peed' (right).

The photograph at the bottom of the second sheet is a comparison view of typical potted plants of 'Frieda Hemple' (left), 'JPD 153-20' (center) and 'Postman Joyner' (right).

The photograph at the top of the third sheet is a comparison view of typical plants of 'JPD 153-20' grown in containers; the plant on the left has not had its tuber de-eyed and the plant on the right has had its tuber de-eyed prior to planting.

The photograph at the bottom of the third sheet is a side perspective view of typical plants of 'JPD 153-20' grown in an open field.

The photograph at the top of the fourth sheet is a close-up view of typical freshly-harvested tubers and roots of 'JPD 153-20'.

The photograph at the bottom of the fourth sheet is a close-up view of a typical inflorescence of 'JPD 153-20'.

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from about 10,000 to 12,000 foot-candles. Plants grown in the shadehouse were nine weeks old and plants grown in the outdoor nursery were eight months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'JPD 153-20'.

Parentage:

*Female, or seed, parent.*—*Caladium×hortulanum* 'Blaze', not patented.

*Male, or pollen, parent.*—*Caladium×hortulanum* 'John Peed', not patented.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description (outdoor nursery-grown plants).*—Appearance: Multi-segmented and somewhat flattened; individual segments ovate to irregular in shape. Height: About 3.4 cm. Diameter: About 4.9 cm to 6.2 cm. Segment height: About 2.4 cm. Segment diameter: About 3 cm. Axillary buds, height: About 4 mm to 6 mm. Texture: Thick, starchy; somewhat brittle. Color: Epidermis, freshly-harvested: Close to 159C; outer skin, close to 199B. Epidermis, dried: Close to 200A. Cortical tissue: Close to 2D. Axillary buds: Close to 36C. Root description: Thick, fleshy contractile roots; color, close to 155C. Rooting habit: Dense.

Plant description:

*Plant type.*—Herbaceous perennial; suitable as a potted plant in containers 15-cm to 25-cm and suitable as a landscape plant in shaded areas.

*Plant and growth habit.*—Compact, short to intermediate in height, upright and uniformly mounded plant habit; moderately vigorous and dense growth habit; rapid growth rate; potted plants in finished or saleable form in about eight to nine weeks after planting tubers; leaf petioles and leaves arise from one or more growing points on tubers; petioles mostly upright and outwardly leaning with development.

*Plant height, from soil level to top of foliar plane, shadehouse-grown potted plants.*—About 28 cm to 34 cm.

*Plant height, from soil level to top of inflorescences, shadehouse-grown potted plants.*—About 43 cm.

*Plant diameter or spread, shadehouse-grown potted plants.*—About 42 cm to 57 cm.

*Number of shoots per plant, shadehouse-grown potted plants, tubers not de-eyed.*—About one to three develop per #1 tuber.

*Number of shoots per plant, shadehouse-grown potted plants, tubers de-eyed*.—About two to three develop per #1 tuber.

*Cataphylls, shadehouse-grown potted plants*.—Length: About 6.5 cm to 9 cm. Width: About 1.5 cm to 1.9 cm. Shape: Lanceolate to wedge-shaped. Apex: Acute. Base: Sheathing the stem. Color, inner surface: Close to 156D; colors and patterns on the outer surface are visible on the inner surface. Color, outer surface: Close to 156D streaked, stippled and tessellated with close to 147A tinged with close to 200A; with development, color becoming closer to 199A and 187B.

Leaf description:

*Arrangement and type*.—Alternate; simple; fancy-type.

*Length, shadehouse-grown potted plants*.—About 23.5 cm to 31 cm.

*Width, shadehouse-grown potted plants*.—About 15 cm to 24.5 cm.

*Shape*.—Broadly ovate, cordate.

*Apex*.—Acute to cuspidate.

*Base*.—Sagittate to peltate.

*Margin*.—Entire; mostly flat with broad undulations.

*Texture, upper and lower surfaces*.—Smooth, glabrous; somewhat rigid.

*Luster, upper surface*.—Glossy; with development and age, leaves become less glossy.

*Luster, lower surface*.—Glaucous, dull sheen.

*Venation pattern*.—Pinnate.

*Color, shadehouse-grown potted plants*.—Developing and fully expanded leaves, upper surface: Midvein and primary veins: Close to 53A tinged with close to 187A. Secondary veins: Close to 183A tinged with close to 53A. Areas surrounding venation: Close to 53A to 53B. Margins: Towards the margins and at the margin, much darker green than 147A. Basal notch: Close to 187C and 53A. Developing and fully expanded leaves, lower surface: Midvein: Close to 185A tinged with close to 53A. Primary veins: Close to 184B to 184C. Areas surrounding venation: Close to 185B and 60A. Interveinal areas: Close to 187C, 189A and 191A. Margins: Narrow margin, close to 187B. Basal notch: Close to 187A.

*Petioles*.—Aspect: Initially upright and straight; with development, leaning outwardly; flexible. Length, shadehouse-grown potted plants: About 21.5 cm to 27 cm. Diameter, distally, shadehouse-grown potted plants: About 4.8 mm to 7 mm. Diameter, proximally, shadehouse-grown potted plants: About 8mm to 12 mm. Texture: Smooth, glabrous; glaucous. Color, shadehouse-grown potted plants: Close to 53A and 60A, variably streaked, stippled and tessellated with close to 200A tinged with close to 147A; below the leaf and petiole junction, close to 60A tinged with close to 53B. Wing length, shadehouse-grown potted plants: About 4.2 cm to 7.4 cm. Wing diameter, shadehouse-grown potted plants: About 8 mm to 12 mm. Texture, inner and outer surfaces: Smooth, glabrous. Luster, inner and outer surfaces: Glossy. Wing color, shadehouse-grown potted plants: Inner surface: Close to 156D; colors and patterns on the outer surface are visible on the inner surface. Outer surface: Close to 156D streaked, stippled and tessellated with close to 147A tinged with close to 200A.

Inflorescence description: Inflorescences observed on nine week-old shadehouse-grown potted plants.

*Inflorescence arrangement*.—Upright hooded spathes surrounding a columnar spadix borne on a tall upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; sweet, jasmine-like with mint-like camphor note.

*Natural flowering season and flower longevity*.—Plants of the new *Caladium* typically flower during the spring and summer in central Florida; flowers develop about nine weeks after growth commences; inflorescences last about three days before fading; inflorescences persistent.

*Spathe*.—Length, overall: About 14.9 cm. Length, distal open portion: About 10 cm. Length, proximal closed portion: About 4.9 cm. Width, distal open portion: About 5.2 cm. Depth, distal open portion: About 1.5 cm. Width, at constriction: About 1.7 cm. Width, proximal closed portion: About 2.9 cm. Shape: Ovate. Apex: Acuminate. Base: Acute. Margin: Entire, variably reflexed. Texture, front and rear surfaces: Smooth, glabrous. Luster, front surface: Dull sheen. Luster, rear surface: Glaucous, dull sheen. Color, front surface: Distal open portion: Close to 155C and 158D; towards the apex, center tinged with close to 145D; with development, color becoming closer to 199C to 199D. Proximal closed portion: Proximally, close to 187A; proximally, close to 187B; color does not change with development. Color, rear surface: Distal open portion: Close to 155C; color does not change with development. Proximal closed portion: Streaked and flushed with close to 182C to 182D, 183B, 187B and 53A with areas and streaks close to 194B and 194C; color does not change with development.

*Spadix*.—Length, overall: About 10.3 cm. Length, male flower zone: About 6.1 cm. Length, sterile zone: About 1.5 cm. Length, female flower zone: About 2.7 cm. Diameter, male flower zone: About 1.4 cm. Diameter, sterile flower zone: About 8 mm. Diameter, female flower zone: About 1.2 cm. Shape: Columnar, spindle-shaped. Apex: Acute. Base: Obtuse. Aspect: Upright. Color, mature, male zone: Close to 158D. Color, mature, sterile zone: Close to 158D. Color, mature, female zone: Close to 158A and 155A. Male flowers: Quantity per spadix: About 288. Shape: Obovate. Height: About 3.2 mm. Diameter: About 3 mm. Pollen amount: Moderate. Pollen color: Close to 4C. Female flowers: Quantity per spadix: About 202. Shape: Obovate. Height: About 2.8 mm. Diameter: About 1.5 mm. Stigma color: Close to 158A. Ovary color: Close to 155A.

*Scape*.—Length: About 28 cm. Diameter: About 9 mm. Strength: Sturdy; flexible. Aspect: Mostly erect. Texture: Smooth, glabrous. Luster: Slightly glossy; glaucous. Color: Distally, densely streaked with close to 53B and 39D; proximally, densely streaked with close to 53B, 39D and 195D; just below spathe, densely streaked with close to 53B and 39D and occasionally streaked with close to 194D.

*Seeds and fruits*.—To date, seed and fruit development have not been observed on plants of the new *Caladium*.

Disease & pest tolerance: Plants of the new *Caladium* have been observed to have above average tolerance to *Xanthomonas* Leaf Spot and to have average tolerance to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment overwinter for re-planting the following spring.

It is claimed:

1. A new and distinct *Caladium* plant named 'JPD 153-20' as illustrated and described.

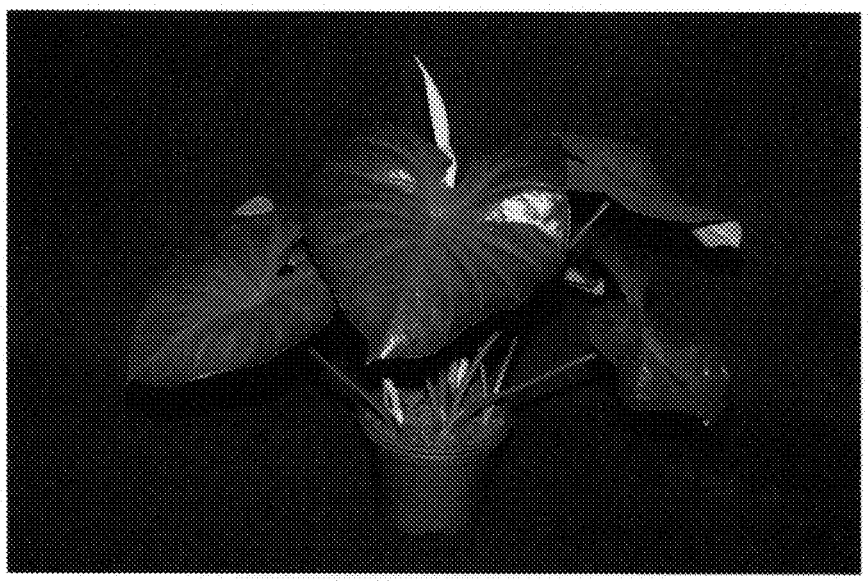

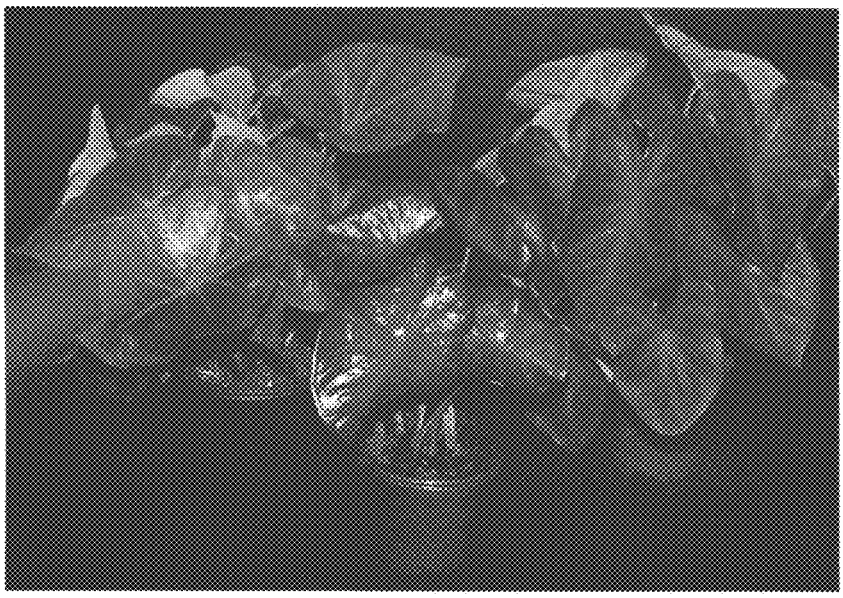
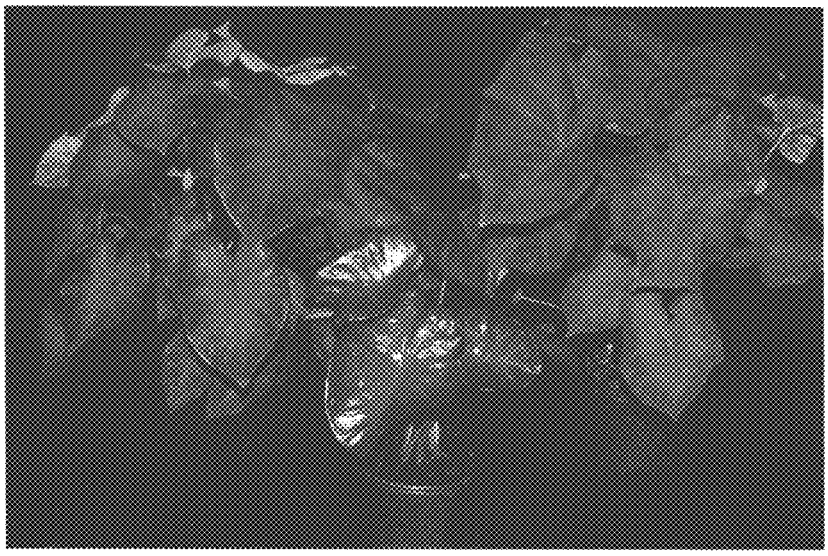

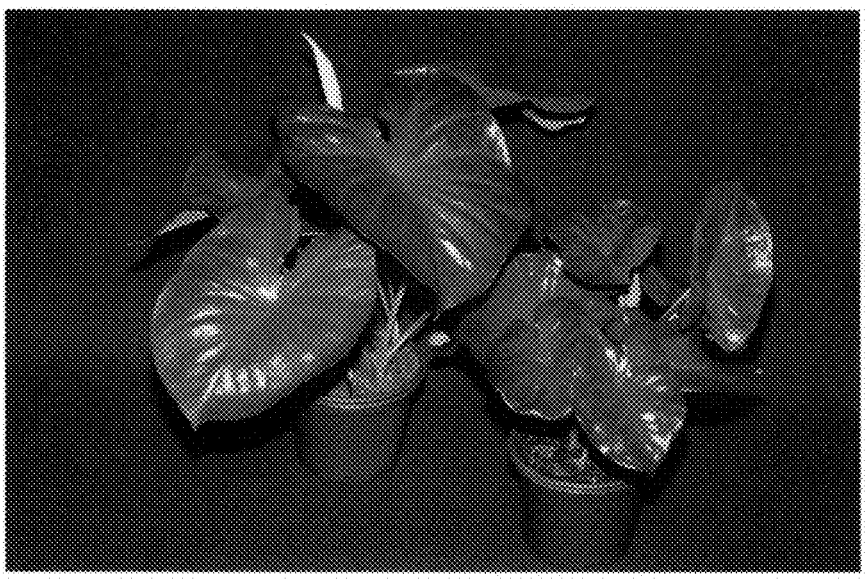
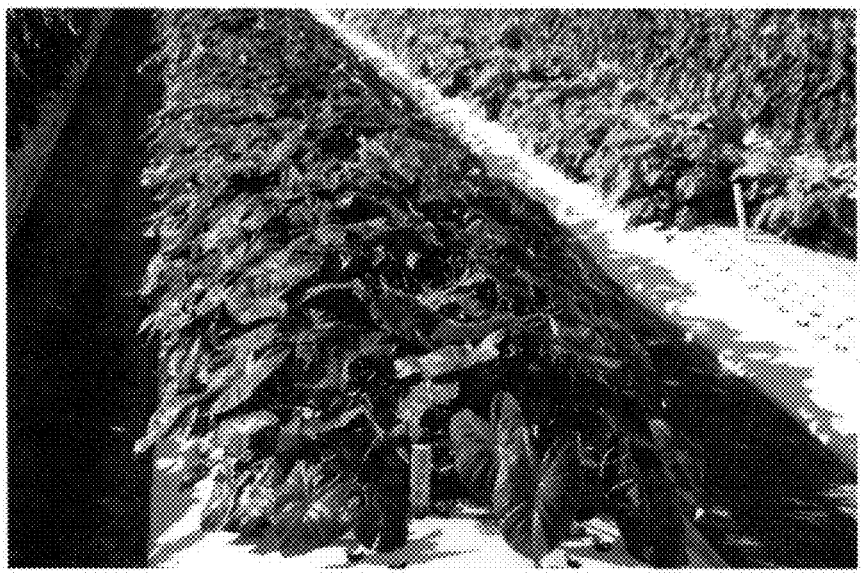

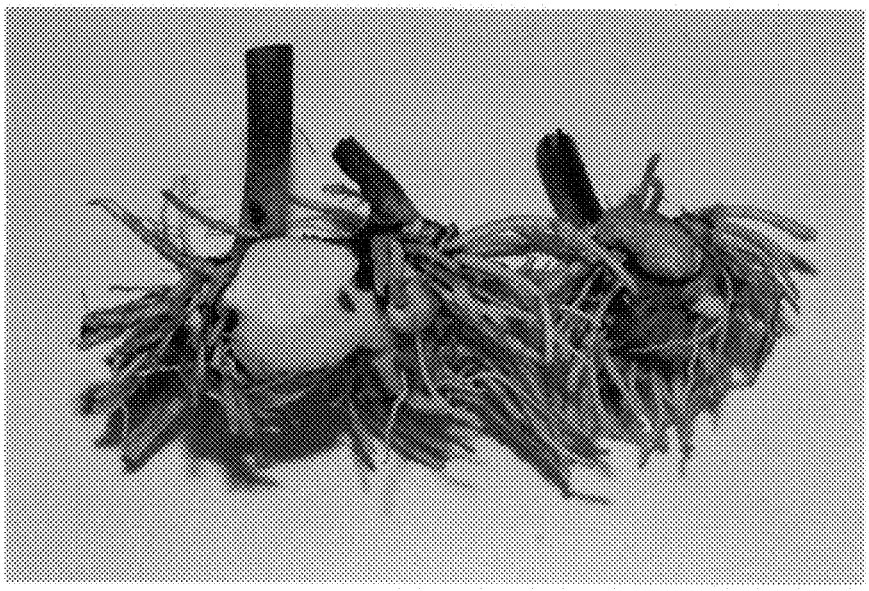
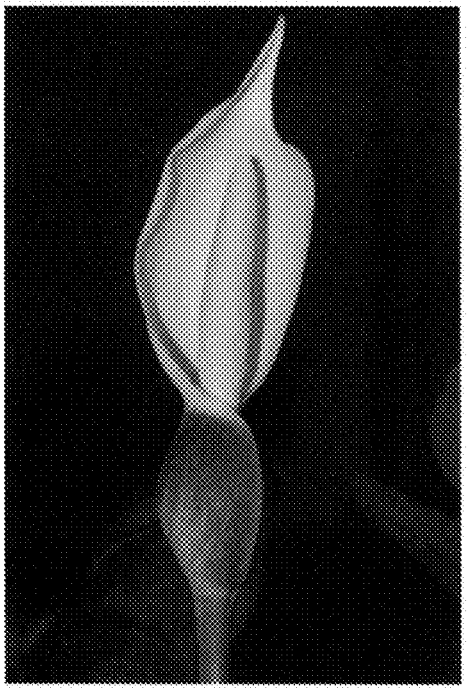

* * * * *